United States Patent
Harris et al.

(10) Patent No.: US 11,464,903 B2
(45) Date of Patent: Oct. 11, 2022

(54) DRUG DELIVERY DEVICE WITH DRIVE ASSEMBLY AND RELATED METHOD OF ASSEMBLY

(71) Applicant: AMGEN INC., Thousand Oaks, CA (US)

(72) Inventors: Justin Harris, Reseda, CA (US); Sudeshna Dutta Ray, Thousand Oaks, CA (US); Jerome Olivas, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 118 days.

(21) Appl. No.: 16/649,058

(22) PCT Filed: Aug. 21, 2018

(86) PCT No.: PCT/US2018/047153
§ 371 (c)(1),
(2) Date: Mar. 19, 2020

(87) PCT Pub. No.: WO2019/074579
PCT Pub. Date: Apr. 18, 2019

(65) Prior Publication Data
US 2020/0289745 A1    Sep. 17, 2020

Related U.S. Application Data

(60) Provisional application No. 62/569,999, filed on Oct. 9, 2017.

(51) Int. Cl.
*A61M 5/142*    (2006.01)
*A61M 5/145*    (2006.01)

(52) U.S. Cl.
CPC ...... *A61M 5/1454* (2013.01); *A61M 5/14248* (2013.01); *A61M 2005/14252* (2013.01);
(Continued)

(58) Field of Classification Search
CPC ...... A61M 2005/14506; A61M 5/1454; A61M 2005/14252; A61M 5/14248;
(Continued)

(56) References Cited

U.S. PATENT DOCUMENTS

2018/0085517 A1 *    3/2018    Laurence ............ A61M 5/1454

FOREIGN PATENT DOCUMENTS

| WO | WO-2014/036239 A2 | 3/2014 |
|----|-------------------|--------|
| WO | WO-2016/145094 A2 | 9/2016 |
| WO | WO-2017/177094 A2 | 10/2017 |

OTHER PUBLICATIONS

International Search Report for International Application No. PCT/US2018/047153, dated Nov. 19, 2018.
(Continued)

*Primary Examiner* — Nathan R Price
*Assistant Examiner* — Justin L Zamory
(74) *Attorney, Agent, or Firm* — Marshall, Gerstein & Borun LLP

(57) ABSTRACT

Drug delivery devices and related methods of assembly are disclosed. The drug delivery device may include a main housing having an exterior surface releasably attachable to a patient, a container disposed in an enclosed space defined by an interior surface of the main housing, and a drive assembly. The container may include a reservoir containing a drug and a stopper. The drive assembly may include drive housing and a tether which slidably engages and is pulled taut against a guide surface of the drive housing. A first end of the tether may be wound around a capstan which is mounted rotatably relative to the drive housing. A second end of the tether may be operably connected to a stopper biasing member. The tether may initially retain the stopper
(Continued)

biasing member in an energized state. When released, the stopper biasing member may expand to move the stopper through the reservoir.

14 Claims, 5 Drawing Sheets

(52) U.S. Cl.
CPC ............ *A61M 2005/14506* (2013.01); *A61M 2205/3334* (2013.01); *A61M 2205/3365* (2013.01)

(58) Field of Classification Search
CPC ............ A61M 2205/3365; A61M 5/20; A61M 5/14244; A61M 2205/353; A61M 5/158
See application file for complete search history.

(56) References Cited

OTHER PUBLICATIONS

Written Opinion of the International Searching Authority for International Application No. PCT/US2018/047153, dated Nov. 19, 2018.

\* cited by examiner

DRUG DELIVERY DEVICE WITH DRIVE ASSEMBLY AND RELATED METHOD OF ASSEMBLY

CROSS-REFERENCE TO RELATED APPLICATION

This is the U.S. national phase of International Patent Application No. PCT/US18/47153, filed Aug. 21, 2018, which claims priority to U.S. Provisional Patent Application No. 62/569,999, filed Oct. 9, 2017. The entire contents of each of the foregoing are expressly incorporated herein by reference.

FIELD OF DISCLOSURE

The present disclosure generally relates to drug delivery devices and, more particularly, the configuration and assembly of a drive assembly for expelling a drug from a reservoir included in a drug delivery device.

BACKGROUND

Automated or semi-automated drug delivery devices are sometimes used to inject a patient with a medicinal fluid or drug. These devices may replace manual drug delivery systems such as syringes, which require a patient or user to provide the motive force necessary to insert a needle or cannula into the patient's tissue and/or expel the drug from a container. Wearable or on-body injectors are one type of drug delivery device that may be used to automate aspects of the drug administration process. Certain patient groups or sub-groups, particularly those having limited dexterity and/or limited experience with self-injection, can benefit from the automation and/or simplification provided by wearable injectors and other types of drug delivery devices.

To provide the actuation energy needed to expel the drug from the container, certain drug delivery devices include an internal drive assembly. Some such drive assemblies incorporate multiple components and/or mechanisms for changing the direction and/or controlling the speed of motion that is output by an internal power source. As a result, some drive assemblies have a relatively large footprint and can increase the overall size of the drug delivery device. In most cases, enlarging the size of the drug delivery device is not desirable. In the context of a wearable injector, for example, a bulky device worn on the patient's skin may impede movement of the patient's limbs. Furthermore, the drive assemblies of certain existing drug delivery devices are relatively complex to assemble, which tends to increase the cost and/or time to manufacture the drug delivery device.

The present disclosure sets forth drug delivery devices and related methods of assembly embodying advantageous alternatives to existing drug delivery devices and methods of assembly, and that may address one or more of the challenges or needs mentioned herein, as well as provide other benefits and advantages.

SUMMARY

One aspect of the present disclosure provides a drug delivery device including a main housing, a container, and a drive assembly. The main housing may include an interior surface defining an enclosed space, and an exterior surface releasably attachable to a patient. The container may be disposed in the enclosed space and include a reservoir containing a drug and a stopper. The drive assembly may include a drive housing, a tether, a capstan rotatable relative to the drive housing about a rotational axis, and a stopper biasing member. The drive housing may possess a guide surface, and the tether may slidably engage the guide surface. Additionally, the tether may have a first end wound around the capstan and a second end operably connected to the stopper biasing member. The stopper biasing member initially may be retained in an energized state by the tether. Furthermore, the stopper biasing member may be configured to expand to move the stopper through the reservoir when released from the energized state. The tether may be pulled taut against the guide surface of the drive housing by the stopper biasing member.

Another aspect of the present disclosure provides a method of assembling a drug delivery device. The method may include: (a) installing a container within a main housing of the drug delivery device, the container having a reservoir containing a drug and a stopper; (b) rotatably connecting a capstan to a drive housing, the capstan being rotatable about a rotational axis; (c) winding a first end of a tether around the capstan; (d) operably connecting a second end of the tether to a stopper biasing member; (e) pulling the tether taut over a guide surface formed by the drive housing; and (f) installing the drive housing within the main housing of the drug delivery device.

An additional aspect of the present disclosure provides a drive assembly for a drug delivery device. The drive assembly may include a drive housing, a tether, a capstan rotatable relative to the drive housing, and a biasing member. The tether may slidably engage the guide surface of the drive housing and having a first end and a second end. The capstan may be rotatably relative to the drive housing about a rotational axis, and the first end of the tether may be wound around the capstan. The biasing member may be operably connected to the second end of the tether. The biasing member may be initially retained in an energized state by the tether and configured to expand to move when released from the energized state. Furthermore, the tether may be pulled taut against the guide surface of the drive housing by the biasing member.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to the configuration and manufacture of an internal drive assembly of a drug delivery device. The drive assembly may be configured to provide the actuation energy necessary for discharging a drug from a reservoir included in the drug delivery device. More particularly, the drive assembly may include a stopper biasing member initially retained in an energized state and, when released, can expand to move a stopper along a longitudinal axis through the reservoir to expel the drug. Additionally, the drive assembly may include a tether configured to restrain or otherwise regulate the expansion of the stopper biasing member. An end of the tether may be wound around a capstan, such as a spindle. The capstan may be selectively rotated in order to create slack in the tether, which in turn permits the stopper biasing member to expand. In order to reduce the overall length or size of the drive assembly, a rotational axis of the capstan may be laterally offset from the longitudinal axis along which the stopper biasing member pushes the stopper. This configuration may require a portion of the tether downstream from the capstan to change directions as the tether is unwound from the capstan. To facilitate this change in directions, the tether may be routed over a stationary or fixed guide surface formed by a drive housing. Furthermore, to improve the manufacturability of the drive assembly, the drive housing may include an opening permitting the capstan to be installed within the drive housing by moving the capstan through the opening at least in a horizontal direction and/or a direction which is perpendicular or otherwise non-parallel to the rotational axis of the capstan. Additionally, the drive housing may be configured to interface with a lock member which temporarily inhibits or prevents unwanted rotation of the capstan during the manufacturing or assembly process. Other benefits and advantages of the presently disclosed drive assembly will be apparent from a review of the description below.

Each of the foregoing components and other components of the drug delivery device and methods of assembling such a device will now be described in more detail.

Figure 1:
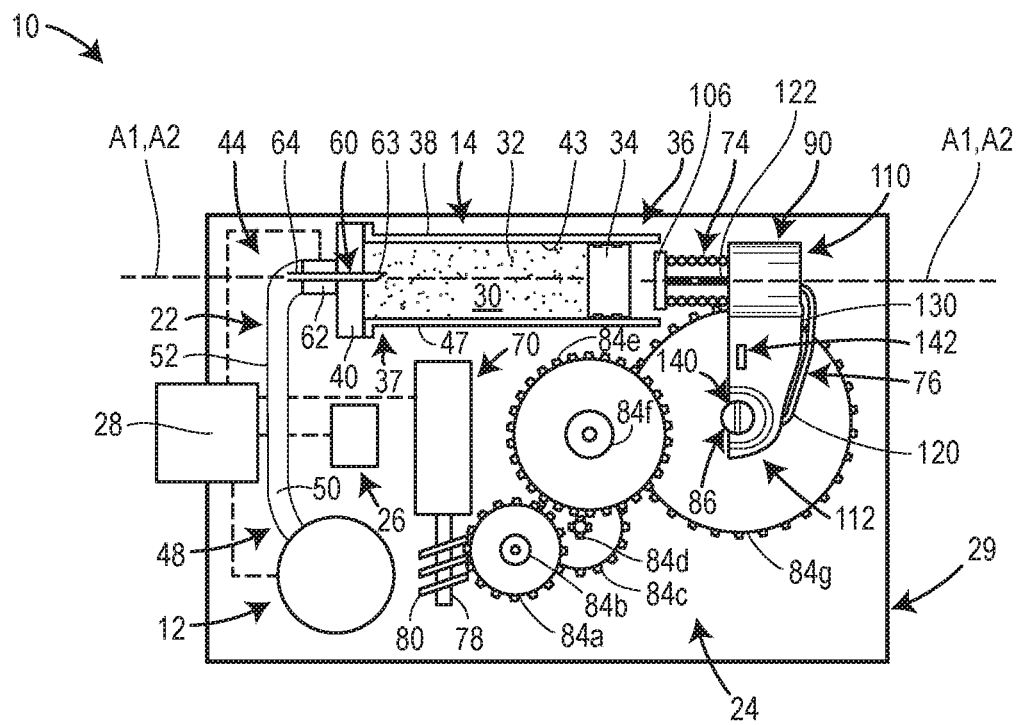
FIG. 1 is schematic top view of an embodiment of a drug delivery device in accordance with principles of the present disclosure.
Figure 2:
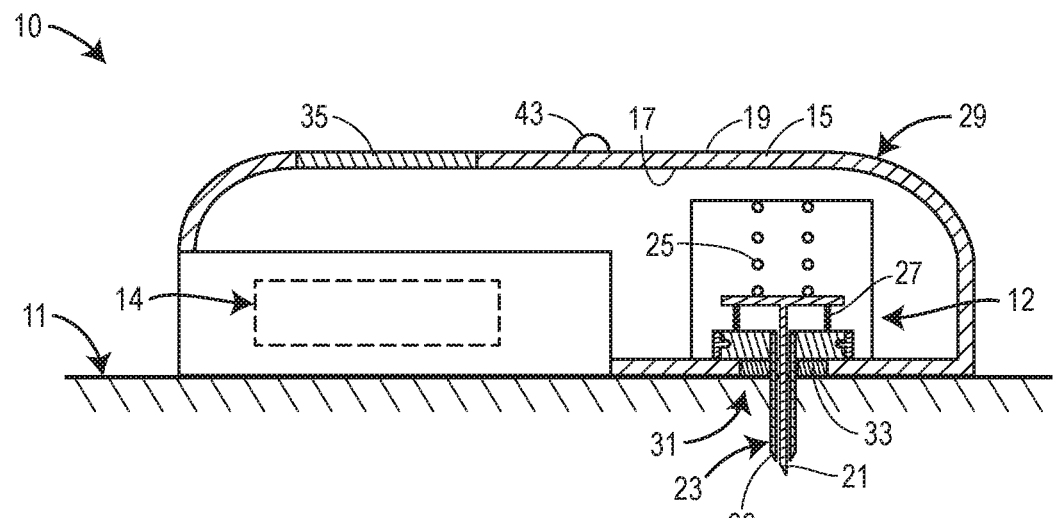
FIG. 2 is a schematic partial cross-sectional side view of the drug delivery device shown in FIG. 1.

FIGS. 1 and 2 are schematic illustrations of an embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, which is releasably attachable to the patient's tissue 11 (e.g., the patient's skin). In other embodiments (not illustrated), the drug delivery device 10 may be configured as an autoinjector, such as an injection pen, which is temporarily held against the patient's tissue 11 over the course of an injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional, caregiver, or other user to administer the injection.

Generally, the drug delivery device 10 may include an insertion mechanism 12, a container 14, a fluid pathway assembly 22, a drive assembly 24, and a controller 26, each of which may be disposed within an interior enclosed space of a main housing 29. An input device 28 (e.g., a user-depressible button, touchscreen, microphone, etc.) may protrude through or otherwise be disposed at an exterior surface 19 of the main housing 29 and may be configured to initiate operation of the drug delivery device 10 by activating, via mechanical and/or electrical means (shown in dotted lines in FIG. 1), the insertion mechanism 12, the fluid pathway assembly 22, the drive assembly 24, the controller 26, and/or other activatable element(s). In order to activate the insertion mechanism 12, the fluid pathway assembly 22, the drive assembly 24, the controller 26, and/or other activatable element(s), the input device 28 may be operably connected to any one of, or any combination of, these elements, directly or indirectly, via mechanical means (e.g., a mechanical linkage or a gear assembly), electrical means, and/or electro-mechanical means. Dotted lines are used in FIG. 1 to schematically illustrate the operational connection between the input device 28 and the insertion mechanism 12, the fluid pathway assembly 22, the drive assembly 24, and the controller 26.

In embodiments where the input device 28 is a button that is depressed or otherwise physically moved by a user or patient, the input device 28 may operate as an actuator that exerts the a motive force needed to activate the insertion mechanism 12, the fluid pathway assembly 22, the drive assembly 24, the controller 26, and/or other mechanisms. In such embodiments, the input device 28 may be physically connected to, either directly or indirectly via a mechanical linkage, the insertion mechanism 12, the drive assembly 24, the fluid pathway assembly 22, and/or other mechanisms, such that manually depressing or otherwise interacting with the input device 28 supplies the motive force necessary to activate the insertion mechanism 12, the drive assembly 24, the fluid pathway assembly 22, and/or other mechanisms. For example, in some embodiments, manually depressing the input device 28 may cause the fluid pathway assembly 22 to move towards the stationary container 14, or alternatively cause the container 14 to move towards the stationary fluid pathway assembly 22, and thereby cause a container access needle to penetrate through a seal member into a reservoir or interior volume of the container 14. Additionally or alternatively, depressing or otherwise interacting with the input device 28 may transmit an electrical and/or mechanical signal to the controller 26, which in turn may execute programmable instructions to control operation of the insertion mechanism 12, the drive assembly 24, and/or the fluid pathway assembly 22. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the input device 28 and which, in response to an electrical control signal received from the controller 26, exerts the motive force needed to activate the insertion mechanism 12, the drive assembly 24, the fluid pathway assembly 22, and/or other mechanisms. One example of such an internal actuator is the rotational power source of the drive assembly 24, which is described in more detail below.

Referring to FIG. 2, the main housing 29 may include a wall 15 having an interior surface 17 and an exterior surface 19. The wall 15 may be a single unitary structure or made of multiple distinct structures interconnected with each other. The interior surface 17 of the wall 15 may define an enclosed space in which the insertion mechanism 12, the container 14, the fluid pathway assembly 22, the drive assembly 24, and the controller 26, and/or other mechanisms and/or components may be disposed. In some embodiments, the enclosed spaced may be sealed shut to define an enclosed clean space having, for example, a sterile or aseptic internal atmosphere. The exterior surface 19 of a bottom portion of the wall 15 may be releasably attachable to the patient's tissue 11. In some embodiments, this may be accomplished with a skin adhesive applied to or otherwise disposed at the exterior surface 19 of the bottom portion of the wall 15 of the main housing 29. In some embodiments, the skin adhesive may be part of an adhesive patch attached to the exterior surface 19 of the bottom portion of the wall 15 of the main housing 29. The exterior surface 19 of a top portion of the wall 15 may include one or more visual indicators 42 (e.g., lights, graphical displays, etc.) and/or a window 35 for viewing the container 14 and the drug 32 contained therein. The one or more visual indicators 42 may be used to communicate information to the user about the operational state of the drug delivery device 10 and/or the condition of the drug 32. An opening 31 may be formed in the bottom portion of the wall 15, and optionally a pierceable sterile barrier 33, such as a pierceable septum, may extend across the opening 31 to seal the interior of the main housing 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and/or plastic. The location of the window 35 on the exterior of the drug delivery device 10 may expose the drug 32 to ambient light including sunlight. Some drugs may be sensitive to certain wavelengths of light and undergo undesirable molecular changes when exposed to such wavelengths of light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the main housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the eye strength of the patient population of the drug 32, among other considerations. Adding the polarized filter to the window 35, in lieu of adding a dark tint to the window 35 and/or shrinking the size of the window 35, advantageously protects the drug 35 from light in the visible range without substantially compromising the ability of the patient or user of the drug delivery device 10 to inspect the drug 32 within the container 14.

After the bottom portion of the wall 15 of the main housing 29 is attached to the patient's tissue 13 (e.g., the patient's skin), the insertion mechanism 12 may be activated to move a subcutaneous delivery member from a retracted position, where a pointed distal end of the subcutaneous delivery member is withdrawn within the main housing 29, to a deployed position, where a pointed distal end projects from the main housing 29 beyond the exterior surface 19 of the main housing 29 (see FIG. 2). In the present embodiment, this may include the insertion mechanism 12 inserting a trocar 21 and a hollow cannula 23 surrounding the trocar 21 through the pierceable sterile barrier 33 and into the patient's tissue 11, as illustrated in FIG. 2. Immediately or shortly thereafter, the insertion mechanism 12 may automatically retract the trocar 21, leaving the distal end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. A distal end 39 of the cannula 23 may be sharpened to a point but may be more blunt than the distal end of the trocar 21. In alternative embodiments (not illustrated), the trocar 21 and cannula 23 may be omitted, and instead the insertion mechanism 12 may insert only a rigid, hollow needle into the patient's tissue 13 for subcutaneous delivery of the drug 32. Also, in any of the above-described embodiments, the subcutaneous delivery member may have a longitudinal axis that is perpendicular to or otherwise non-parallel to a longitudinal axis A1 of the container 14.

Still referring to FIG. 2, in some embodiments the insertion mechanism 12 may include an insertion biasing member 25 and a retraction biasing member 27. Prior to activation of the insertion mechanism 12, each of the insertion biasing member 25 and the retraction biasing member 27 may be retained in an energized state. Upon activation of the insertion mechanism 12 via, e.g., the input device 28, the insertion biasing member 25 may be allowed to expand or otherwise release its stored energy, thereby moving the subcutaneous delivery member from the retracted position to the deployed position. In the illustrated embodiment, expansion of the insertion biasing member 25 causes the trocar 21 and the cannula 23 to move from their retracted position, where their distal ends are located within the main housing 29, to their deployed position shown in FIG. 2, where their distal ends are located outside of the main housing 29. The retraction biasing member 53 may be retained in its energized state during the insertion procedure. Subsequent to the insertion procedure, the retraction biasing member 53 may release its stored energy and expand to move the trocar 21 from the deployed position back to the retracted position, leaving the cannula 23 in the deployed position.

In the embodiment illustrated in FIG. 2, the insertion biasing member 25 and the retraction biasing member 27 are respective compression springs which are arranged concentrically with each other. Other power sources for the insertion biasing member 25 and/or the retraction biasing member 27 are also possible, including, for example, a torsion spring, an electric motor, a hydraulic or pneumatic pump, or a canister that releases a pressurized gas or a pressurized liquid to provide actuation energy. In some embodiments, the insertion biasing member 25 and the retraction biasing member 27 may be defined by a single electric motor which is operated in a forwards and a reverse direction to provide the insertion and retraction movements. Also, in some embodiments, the retraction biasing member 27 may be omitted.

Referring back to FIG. 1, the container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the main housing 29 such that the container 14 cannot move relative to the main housing 29; whereas, in other embodiments, the container 14 may be slidably connected to the main housing 29 such that the container 14 can move relative to the main housing 29 during operation of the drug delivery device 10. The container 14 may have an elongate, barrel-like or cylindrical shape extending along a longitudinal axis A1. In embodiments where the drug delivery device 10 is configured as an on-body injector, the longitudinal axis A1 of the container 14 may be perpendicular or substantially perpendicular, or otherwise non-parallel, to a direction in which the insertion mechanism 12 inserts the subcutaneous delivery member such as the cannula 23 into the patient. This configuration may allow the on-body injector to have a generally planar, low-profile shape that can be worn by the patient without substantially impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14 to expel the drug 32 container therein.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 30 may be completely or partially filled with the drug 32. The drug 32 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive assembly 24 may push the stopper 34 along the longitudinal axis A1 through the reservoir 30 from the proximal end 36 of the container 14 to a distal end 37 of the container 14 in order to expel the drug 32. As described below in more detail, the drive assembly 24 may include a rotational power source, a gear module configured to convert the rotational speed and/or torque of the rotational movement output by the rotational power source, a stopper biasing member initially retained in an energized state and configured to axially expand to move the stopper through the reservoir 30, and a tether configured to restrain or otherwise regulate the expansion of the stopper biasing member.

At the distal end 37 of the container 14, an opening 45 may be formed in the wall 38. At least prior to operation of the drug delivery device 10, the opening 45 may be covered and sealed closed by a seal member 40, such as a pierceable septum, connected to the distal end 37 of the container 14. A proximal end surface of the seal member 40 and the interior surface 43 of the wall 38 of the container 14 may define the reservoir 30. Additionally, in some embodiments, a distal end surface of the stopper 34 may define the reservoir 30.

Generally, the seal member 40 may be configured to selectively permit access to the reservoir 30. During operation of the drug delivery device 10, the seal member 40 may be physically altered (e.g., pierced) to permit fluid communication with the drug 32 in the reservoir 30. In some embodiments, the seal member 40 may be constructed of a flexible or elastically deformable material such as rubber, for example, which is capable of being penetrated or pierced by a sharpened end or point 63 of a container access needle 60 of the fluid pathway assembly 22. In some embodiments, the seal member 40 may be clamped or otherwise secured to the distal end surface of the wall 38 of the container 14 by a fastener (e.g., a crimp ring) and/or adhered directly to the distal end surface of the wall 38 of the container 14.

Still referring to FIG. 1, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive assembly 24 may move the stopper 34 in the distal direction relative to the wall 38 of the container 14 to force the drug 32 stored in the container 14 through the sterile fluid flow path of the fluid pathway assembly 22 and into the cannula 23 or needle or other delivery member of the insertion mechanism 12 for subcutaneous delivery to the patient.

In some embodiments, the fluid pathway assembly 22 may be rigidly connected to the wall 15 of the main housing 29 such that the fluid pathway assembly 22 cannot move relative to the main housing 29; whereas, in other embodiments, the fluid pathway assembly 22 may be slidably or moveably connected to the wall 15 of the main housing 29 such that the fluid pathway assembly 22 can move relative to the main housing 29 during operation of the drug delivery device 10. In the former embodiments, the container 14 may be slidably or moveably connected to the wall 15 of the main housing 29 such that the seal member 40 can be moved toward and pierced by the point 63 of the stationarily arranged container access needle 60 of the fluid pathway assembly 22. In the latter embodiments, the container 14 may be stationarily positioned relative to the main housing 29 while the fluid pathway assembly 22 is moved toward the container 14, causing the point 63 of the container access needle 60 to pierce through the seal member 40 and access the reservoir 30.

The fluid pathway assembly 22 may include a first end 44 connected to the container 14, a second end 48 connected to the insertion mechanism 12, and a fluid passage 50 extending between the first end 44 and the second end 48. The fluid passage 50 may be sterilized, and may be partially or entirely made of a flexible tubing 52. Initially, there may be slack in the flexible tubing 52 to allow the fluid pathway assembly 22 to move relative to the main housing 29 and/or to allow components of the insertion mechanism 12 to which the fluid pathway assembly 22 is attached to move relative to the main housing 29. In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element made be made of metal, whereas the flexible tubing 52 may be made of a polymeric material such as plastic.

Still referring to FIG. 1, the first end 44 of the fluid pathway assembly 22 may include the container access needle 60 and a connection hub or mounting member 62. The container access needle 60 may have a sharpened end or point 63, corresponding to a proximal end of the container access needle 60, and a distal end 64 in fluid communication with the fluid passage 50. The mounting member 62 may cover a length of the distal end 64 of the container access needle 60 and connect the distal end 64 of the container access needle 60 to the flexible tubing 52. In some embodiment, during activation of the drug delivery device 10, the input device 28 may translate, rotate, or otherwise move the mounting member 62 relative to the main housing 29, thereby causing the container access needle 60 to move from a storage position, where the proximal end 63 of the container access needle 60 is exterior to the reservoir 30, to an operational position, where the proximal end 63 of the container access needle 60 is disposed within the reservoir 30 and in fluid communication with the drug 32 (see FIG. 1)

More particularly with respect to the container access needle 60, it may possess a hollow, tubular shape with one or more openings at each of the proximal end 63 and the distal end 64. The container access needle 60 made be constructed of a rigid material including, but not limited to, metal (e.g., stainless steel) and/or plastic. In some embodiments, the mounting member 62 may be constructed of a different material than the container access needle 60 such that the mounting member 62 and the container access needle 60 are separate, but rigidly connected, components. In some embodiments, the mounting member 62 may be constructed of a rigid plastic material whereas the container access needle 60 may be constructed of metal. In other embodiments, the mounting member 62 and the container access needle 60 may be made of the same material such that they form a single, unitary one-piece structure.

In some embodiments, displacing the input device 28 may cause the simultaneous or substantially simultaneous activation of the insertion mechanism 12, the fluid pathway assembly 22, the drive assembly 24, the controller 26, and other activatable element(s) of the drug delivery device 10, or any combination thereof. In other embodiments, displacing the input device 28 may cause the insertion mechanism 12, the fluid pathway assembly 22, the drive assembly 24, the controller 26, and other activatable element(s) to activate in a predetermined sequential order.

With continued reference to FIG. 1, and now additionally FIGS. 3-9, further description of the drive assembly 24 is provided. In some embodiments, the drive assembly 24 may be activated in response to a mechanical and/or electrical signal generated by the users depression or other interaction with the input device 28; whereas, in other embodiments, the drive assembly 24 may be activated in response to an electrical signal received from the controller 26. Furthermore, in some embodiments, in addition to activating the drive assembly 24, the controller 26 may monitor and/or control the operation of the drive assembly 24 in order to regulate the rate and/or timing with which the stopper 34 expels the drug 32 from the reservoir 30.

In some embodiments, the drive assembly 24 may include a rotational power source 70 configured to output rotational movement, a gear module 72 configured to convert the speed and/or torque of the rotational movement output by the rotational power source 70, a stopper biasing member 74 initially retained in an energized state and configured to axially expand to move the stopper 34 through the reservoir 30, a tether 76 configured to restrain or otherwise regulate the expansion of the stopper biasing member 74, a capstan 86 around which an end of the tether 76 is initially wound, and a drive housing 90 for operably connecting the capstan 86 and the stopper biasing member 74 to each other and/or the main housing 29.

The rotational power source 70 may be any mechanism capable of converting stored energy into rotational mechanical motion, including, but not limited to, an electric motor, a torsion spring, and/or a hydraulic or pneumatic pump. In the case of an electric motor, the drug delivery device 10 may include a battery for storing electrical energy for use by the rotational power source 70. The rotational power source 70 may possess a rotatable output shaft 78 for transferring rotational motion to the gear module 72. As shown in FIG. 1, a screw or worm gear 80 may be mounted on and axially aligned with the output shaft 78, and include spirally-cut teeth which meshingly engage with teeth of one of the spur gears included in the gear module 72. During operation, the worm gear 80 may rotate relative to the mounting plate 82 of the gear module 72. In some embodiments, the rotational power source 70 may be mounted to the wall 15 of the main housing 29 separately or independently of the gear module 72; whereas, in other embodiments, the rotational power source 70 may be pre-attached directly to the gear module 72 such that mounting the gear module 72 to the wall 15 of the main housing 29 results in mounting the rotational power source 70 within the main housing 29. In such latter embodiments, the rotational power source 70 and the gear module 72, though separate components, may be installed in the main housing 29 as a single unit. Furthermore, in alternative embodiments, a bevel gear may be substituted for the worm gear 80.

In some embodiments, the worm gear 80 may have a self-locking configuration, such that the worm gear 80 can drive the gear 84a but the gear 84a cannot drive (or will have extreme difficulty driving) the worm gear 80. The self-locking configuration may depend on a lead angle, a pressure angle, and/or a coefficient of friction between the worm gear 80 and the gear 84a. The self-locking configuration of the worm gear 80 may, via the tether 76, help prevent premature expansion or creep of the stopper biasing member 74 prior to operation of the rotational power source 70.

Referring to FIG. 1, the gear module 72 generally functions as a gearbox and may include a mounting plate 82 and a plurality of gears 84a-g. Each of the gears 84a-g may be rotatably connected to the mounting plate 82 such that each of the gears 84a-g can rotate relative to the mounting plate 82. In some embodiments, the rotatable connection for any individual one of the gears 84a-g may be achieved by a pin or shaft which is rigidly attached to the gear and slidably received in a groove or recess formed in a top surface of the mounting plate 82. In some embodiments, each gear of the gears 84a-g may be a spur gear having a plurality of a teeth either straight or helically cut into an outer circumferential surface of the gear. The teeth of each gear of the plurality of gears 84a-g may meshingly engage with the teeth of at least one other gear of the plurality of gears 84a-g during operation of the rotational power source 70. The gear 84a, which may function as the input gear of the gear module 72, may have teeth which meshingly engage with the teeth of the worm gear 80 such that the gear 84a receives rotational power from the rotational power source 70. The gear 84g, which may function as the output gear of the gear module 72, may be directly or indirectly connected to and/or axially aligned with a capstan 86 such that the gear 84g turns or otherwise outputs rotational movement to the capstan 86. Due to a gear reduction provided by the gear module 72, the rotational movement output to the capstan 86 may have a lower rotational speed and, in some cases, a higher torque, than the rotational movement output by the rotational power source 70. The gear reduction may be achieved by configuring at least some of the gears 84a-g with different outer diameters and/or different numbers of teeth.

Certain pairs of the gears 84a-g may be arranged in parallel, that is sharing a common rotational axis; whereas other pairs of the gears 84a-g may be arranged in series, that is having rotational axes that are offset and parallel to each other yet still having teeth that meshingly engage each other. As illustrated in FIG. 1, the following gear pairs may be arranged in parallel: (i) gears 84a and 84b; (ii) gears 84c and 84d; and (iii) gears 84e and 84f. By contrast, the following gear pairs may be arranged in series: (i) gears 84b and 84c; (ii) gears 84d and 84e; and (iii) gears 84f and 84g. In some embodiments, the number of gear pairs arranged in series may be equal to three, or less than three in other embodiments, in an effort to reduce components and increase reliability. The worm gear 80 and the spur gear 84a are also a gear pair that may be arranged in series.

Figure 3:
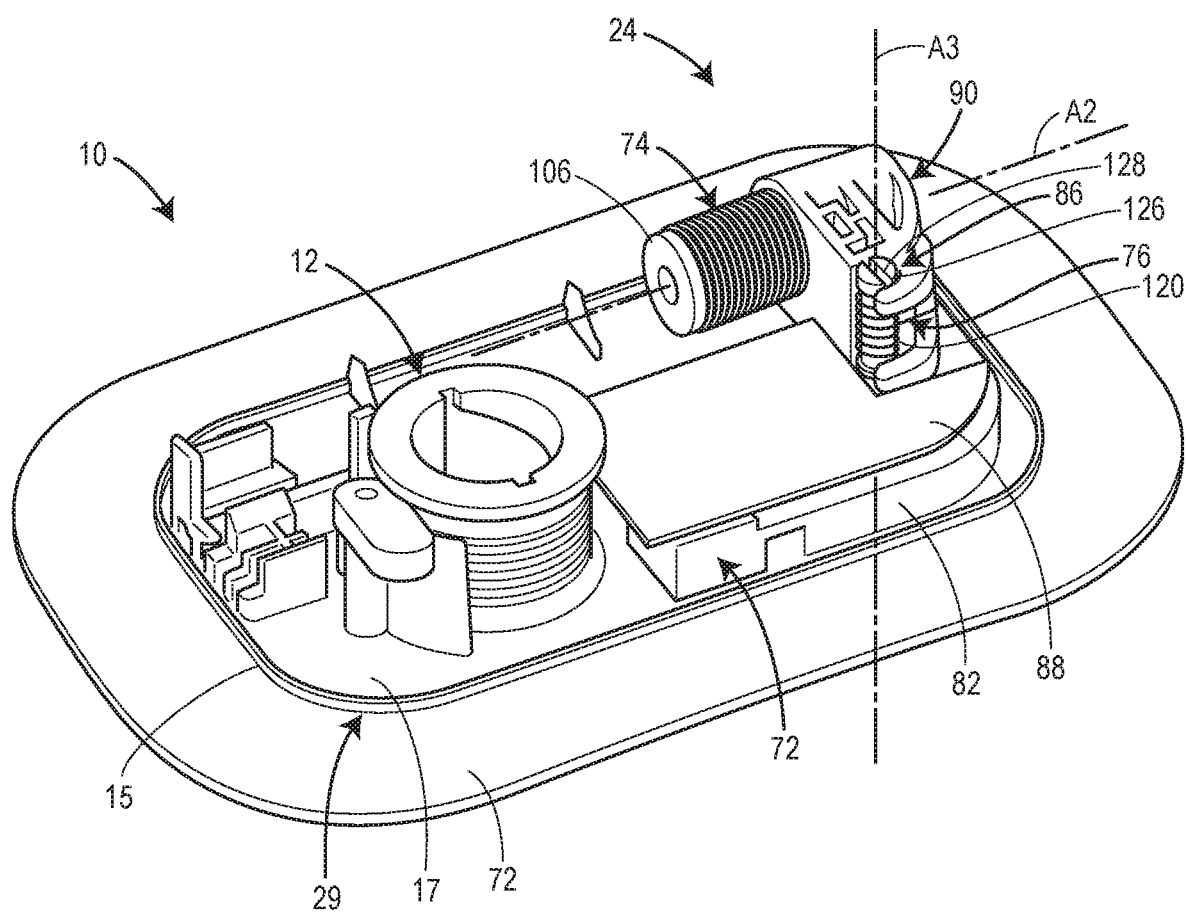
FIG. 3 is a perspective view of the drug delivery device of FIG. 1, with several components omitted including the container, fluid pathway assembly, and top portion of the wall of the main housing.

As seen in FIG. 3, the mounting plate 82 may be connected to, but separate from, the wall 15 of the main housing 29. In some embodiments, the mounting plate 82 may be connected to the wall 15 via a fastener such as a screw or bolt, for example. By virtue of being mounted on the mounting plate 82, the gears 84a-g are not directly connected to the wall 15 of the main housing 29. Accordingly, bending or other deformations to the wall 15 of the main housing 29 are less likely to affect the alignment of the gears 84a-g. In some embodiments, the mounting plate 82 may be constructed of a more rigid material and/or thicker material than the wall 15 of the main housing 29, so as to render the mounting plate 82 less susceptible to bending than the wall 15 of the main housing 29. Furthermore, since the mounting plate 82 provides a rigid support structure for the gears 84a-g, there may be more design freedom with respect to the shape and/or materials used construct the wall 15 of the main housing 29. Additionally, a printed circuit board 88 associated with the controller 26 may be connected directly to the mounting plate 82, instead of to the wall 15, as shown in FIG. 3.

Referring to FIGS. 1 and 3, the drive assembly 24 may include one or more components for operationally connecting the gear module 72 to the stopper 34. In some embodiments, these components may include the capstan 86, the tether 76, the stopper biasing member 74, the drive housing 90, and/or other components. The stopper biasing member 74 may be initially retained in an energized state by the tether 76. When it is released from its energized state, the stopper biasing member 74 may move the stopper 34 in the distal direction along the longitudinal axis A1 through the reservoir 30, thereby expelling the drug 32 from the container 14 via the container access needle 60. In some embodiments, the stopper biasing member 74 may be configured to expand in length along a linear longitudinal axis A2. In the present embodiment, the longitudinal axis A2 of the stopper biasing member 74 is coextensive with the longitudinal axis A1 of the container 14, as shown in FIG. 1.

In some embodiments, the stopper biasing member 74 may be an elastically deformable element such as a spring which is configured to store mechanical energy when deformed from its original shape, and release that mechanical energy in the form of a motive force when returning to its original shape. In the illustrated embodiment, the stopper biasing member 74 includes a compression spring 100 having a helical coil centered about the longitudinal axis A2. While the illustrated embodiment includes only a single compression spring, alternative embodiments of the stopper biasing member 74 may include two or more compression springs, which, in some cases, can be concentrically arranged relative to each other. The compression spring 100 may have a proximal end 102 which abuts directly against a first end 110 of the drive housing 90, and a distal end 104 which abuts directly against a tether mounting member 106. In this way, the first end 110 of the drive housing 90 may define a first spring seat and the tether mounting member 106 may define a second spring seat. Prior to operation, the stopper biasing member 74 may be axially compressed between the first end 110 of the drive housing 90 and the tether mounting member 106. To prevent the stopper biasing member 74 from expanding when in this compressed or energized state or configuration, the tether 76 may be used to prevent the tether mounting member 106 from moving in the distal direction away from the first end 110 of the drive housing 90. This may be accomplished by threading the tether 76 through a central opening of the compression spring 100, connecting a second end 122 of the tether 76 to tether mounting member 106, and removing any slack from the tether 76 such that the tether 76 is placed under tension. In this way, the second end 122 of the tether 76 may be operably connected to the stopper biasing member 74 via the tether mounting member 106. In alternative embodiments, the tether mounting member 106 may be omitted, and the tether 76 may be operably connected to the stopper biasing member 74 via a direct connection between the second end 122 of the tether 76 and the distal end 104 of the stopper biasing member 74.

It should be understood that the stopper biasing member 74 is not limited to a compression spring or other spring-loaded configurations. In alternative embodiments, stopper biasing member 74 may include a pneumatic or hydraulic cylinder powered by, for example, a source of compressed gas or liquid. Other configurations of the stopper biasing member 74 are also possible.

Figure 4:
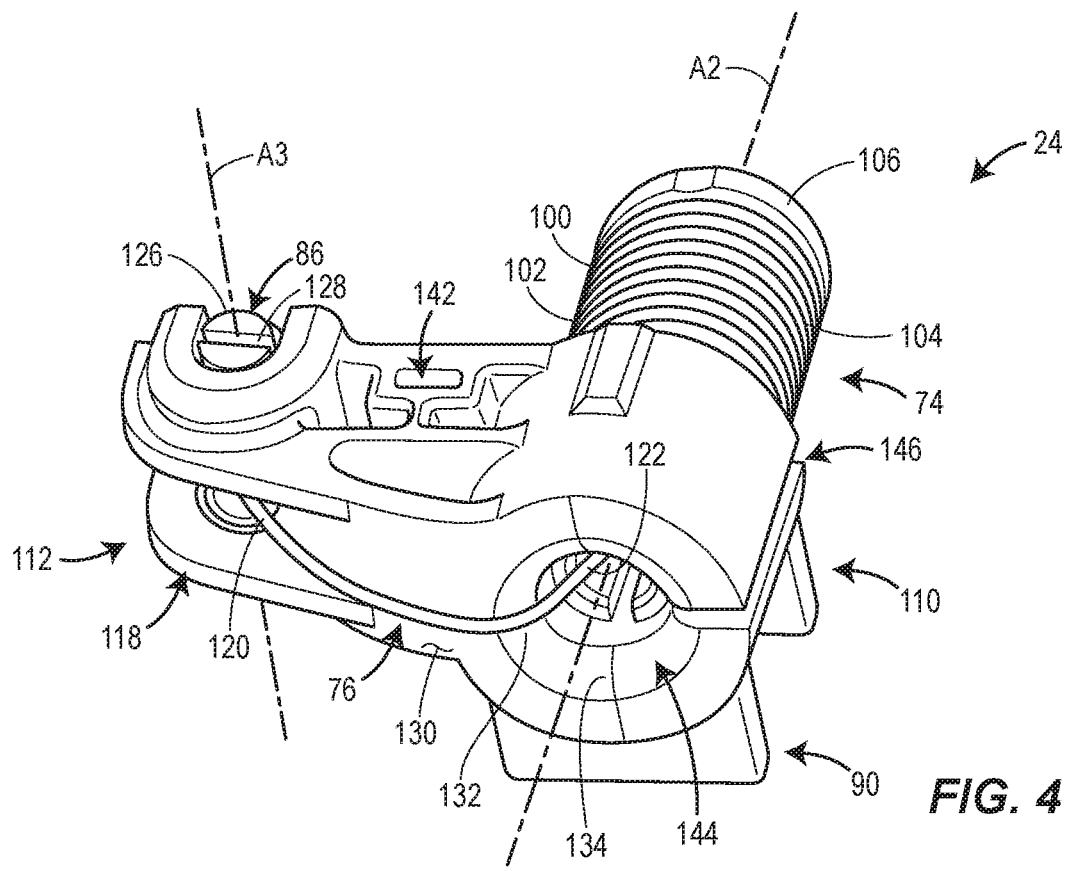
FIG. 4 is a front perspective view of the drive assembly depicted in FIG. 3.
Figure 5:
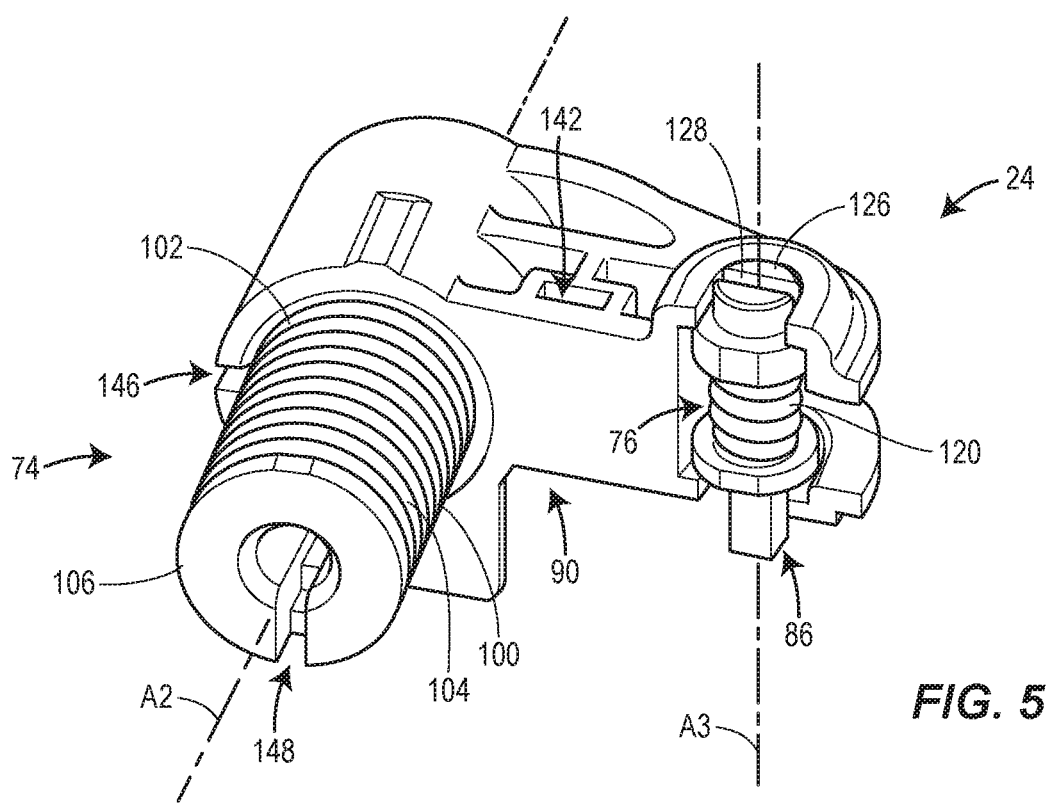
FIG. 5 is a rear perspective view of the drive assembly depicted in FIG. 4.

Referring to FIGS. 3-5, the capstan 86 may be rotatable relative to the drive housing 90 and/or the main housing 29 about a rotational axis A3. The capstan 86 may be arranged such that the rotational axis A3 is laterally offset or spaced apart from the longitudinal axis A2 of the stopper biasing member 74. Accordingly, an overall length of the drive assembly 24 may be reduced, as compared to a configuration where the capstan 86 is positioned directly proximal to the stopper biasing member 74.

The capstan 86 may take the form of a winch, spindle, drum, winch drum, wheel, axle, rod, and/or any other rotatable member around which a first end 120 of the tether 76 can be wound. In some embodiments, such as the one illustrated in FIG. 3, the capstan 86 may include a cylindrical outer surface around which the first end 120 of the tether 76 can be wrapped. The capstan 86 may be partially or entirely housed within the drive housing 90. In some embodiments, the capstan 86 may be rotatably connected to or supported by an inwardly facing or interior surface 116 of first end 110 of the drive housing 90. This rotatable connection may be achieved, for example, via a plurality of bearings that roll against the interior surface 116 of the first end 110 of the drive housing 90 and an exterior surface of the capstan 86. In such embodiments, the interior surface 116 may be curved in such a manner as to correspond to the curvature of the exterior surface of the capstan 86. In alternative embodiments, the capstan 86 may rotate relative to drive housing 90, but may not necessarily be rotatably connected to or supported by the drive housing 90. In such alternative embodiments, the capstan 86 may be rotatably connected directly to the wall 15 of the main housing 29.

The rotational power source 70 may be operably connected to the capstan 86 and configured to selectively rotate the capstan 86 to create slack in the tether 76 to regulate or control expansion of the stopper biasing member 74. In this way, the tether 76 enables a braking functionality. In some embodiments, the rotational power source 70 may be operably connected to the capstan 86 via the gears 84a-g. In one implementation, the capstan 86 may be rigidly mounted on the output gear 84 such that the two components jointly rotate together about the rotational axis A3. In another implementation, the rotational axis A3 of the capstan 86 may be laterally offset from the rotational axis of the output gear 84, and the capstan 86 may include circumferentially-arranged gear teeth which meshingly engage with the gear teeth of the output gear 84g.

Figure 8:
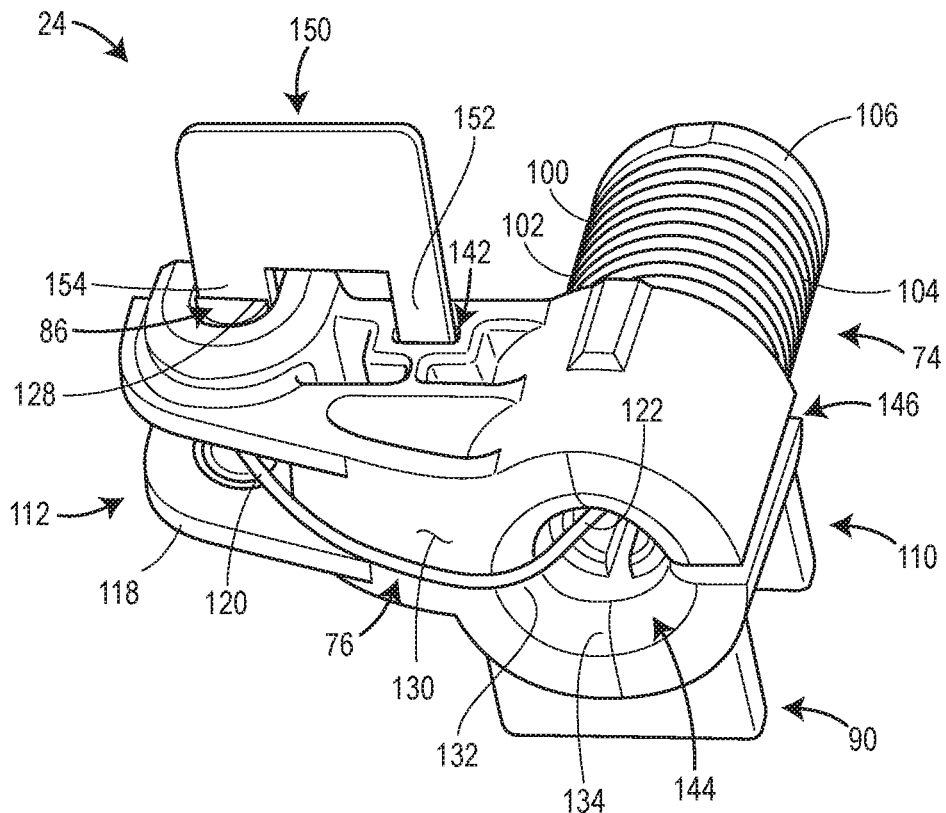
FIG. 8 is a perspective view of the drive assembly depicted in FIG. 4, installed with a lock member.

As shown in FIGS. 3-5, an upper end of the capstan 86 may include an upwardly facing end surface 126. Generally, the end surface 126 may face in a direction away from the output gear 84g when the capstan 86 and output gear 84g are installed within the main housing 29. Furthermore, the upwardly facing end surface 126 of the capstan 86 may be perpendicular or otherwise non-parallel to the rotational axis A3. An opening 128 may be formed in the upwardly facing end surface 126 of the capstan 86, and may be centered generally about the rotational axis A3. As described below in more detail, the opening 128 may be configured to receive and engage an end of a lock member 150 for temporarily limiting (e.g., preventing) rotation of the of the capstan 86 relative to the drive housing 90 during assembly of the drug delivery device 10, as illustrated in FIG. 8. In some embodiments, the opening 128 may extend into the capstan 86 in a direction that this parallel or otherwise non-perpendicular to the rotational axis A3 of the capstan 86. In some embodiments, the opening 128 may be a through hole that extends through the entirety of the capstan 86 and exits through bottom end of the capstan 86. In other embodiments, the opening 128 may be a recess, groove, depression, or blind hole formed in the upwardly facing end surface 126. Furthermore, the opening 128 need not necessarily be formed in the upwardly facing end surface 126 of the capstan 86. In some embodiments, the opening 128 may be formed in a side surface and/or a downwardly facing surface of the capstan 86.

The tether 76 may be any flexible elongate member such as a cord, wire, and/or chain, for example. The tensile strength of the tether 76 may be substantially greater than the compressive strength of the tether 76. As described above, prior to drug delivery, a length of the first end 120 of the tether 76 may be wound around the capstan 86, whereas the second end 122 of the tether 76 may be operably connected to the stopper biasing member 74 via the tether mounting member 106. In this configuration, the tether 76 may be pulled taut under substantial tension between the capstan 86 and the tether mounting member 106 to hold the stopper biasing member 74 in a compressed or energized state. During drug delivery, the rotational power source 70 may, via the gears 84a-g, rotate the capstan 86 in a direction causing the first end 120 of the tether 76 to unwind from the capstan 86. As a result, slack may be created in tether 76, which may allow the stopper biasing member 74 to elastically expand and return (partially or entirely) to its original state or shape.

As the stopper biasing member 74 expands, it may pull the tether 76 along with it. Because the rotational axis A3 of the capstan 86 is laterally offset or spaced apart from the longitudinal axis A2 of the stopper biasing member 74, the tether 76 may need to change directions as it travels from the capstan 86 to the stopper biasing member 74. To facilitate this change in directions, a portion of the tether 76 may be routed over and pulled taut against a guide surface 130 formed by the drive housing 90. The guide surface 130 may remain stationary relative to the main housing 29 as the tether 76 slides over the guide surface 130. Also, the guide surface 130 may be relatively smooth in order to limit any sliding friction between the tether 76 and the guide surface 130. A stationary guide surface 130 advantageously reduces the number of moving parts required by the drive assembly 24, as compared to a drive assembly that, for example, employs a pulley member mounted rotatably relative to the drive housing. With less moving parts, the presently disclosed drive assembly may be more reliable and/or less complex to assemble.

In some embodiments, the guide surface 130 may be configured to transition the tether 76 from a first direction to a second direction, wherein the second direction is perpendicular or otherwise non-parallel to the first direction. As such, a first portion of the tether 76 travelling upstream of the guide surface 130 may move in the first direction, while a second portion of the tether 76 travelling downstream of the guide surface 130 may move in a second direction. In some embodiments, the first direction and/or the second direction may be perpendicular or otherwise non-parallel to the rotational axis A3 of the capstan 86, and the second direction may be parallel or otherwise non-perpendicular to the longitudinal axis A2 of the stopper biasing member 74.

As depicted in FIG. 4, the guide surface 130 may be part of an exterior surface 118 of the drive housing 90, such that the tether 76 is pulled taut against an outer periphery of the drive housing 90. Furthermore, the guide surface 130 may be positioned and/or extend between the first end 110 and the second end 112 of the drive housing 70. Also, the guide surface 130 may be formed on a side of the drive housing 90 that is opposite to a side of the drive housing 90 which abuts against the stopper biasing member 74. In some embodiments, the drive housing 90 may be a single, integrally-constructed unitary structure and the guide surface 130 may be one of the surfaces of that structure. In other embodiments, the drive housing may be made of multiple distinct structures rigidly interconnected with each other, and the guide surface 130 may be a surface of one of those distinct structures.

Still referring to FIG. 4, the guide surface 130 may be contoured or curved to change the direction of the tether 76. In the present embodiment, a portion of the guide surface 130 closest to the second end 112 of the drive housing 90 or the capstan 86 possesses a generally convex curvature. A portion of the guide surface 130 closest to the first end 110 of the drive housing 90 or the stopper biasing member 74 is defined by a rounded corner 132, where two perpendicular or substantially perpendicular faces of the drive housing 90 intersect. In alternative embodiments, the corner 132 may be chamfered in addition to, or as an alternative to, being rounded. In the embodiment shown in FIG. 4, the corner 132 is formed by a rim 134 of a generally circular opening 144 formed in the first end 110 of the drive housing 90. As described below, the tether 76 is fed through the opening 144 during expansion of the stopper biasing member 74.

While the guide surface 130 of the present embodiment is relatively wide and long, the present disclosure is not limited to such a configuration of the guide surface. In alternative embodiments, for example, the guide surface may be formed by a cylindrical pin which is held stationary relative main housing 29, and defines a relatively short and/or narrow guide surface as compared to the guide surface 130 illustrated in the figures.

Figure 6:
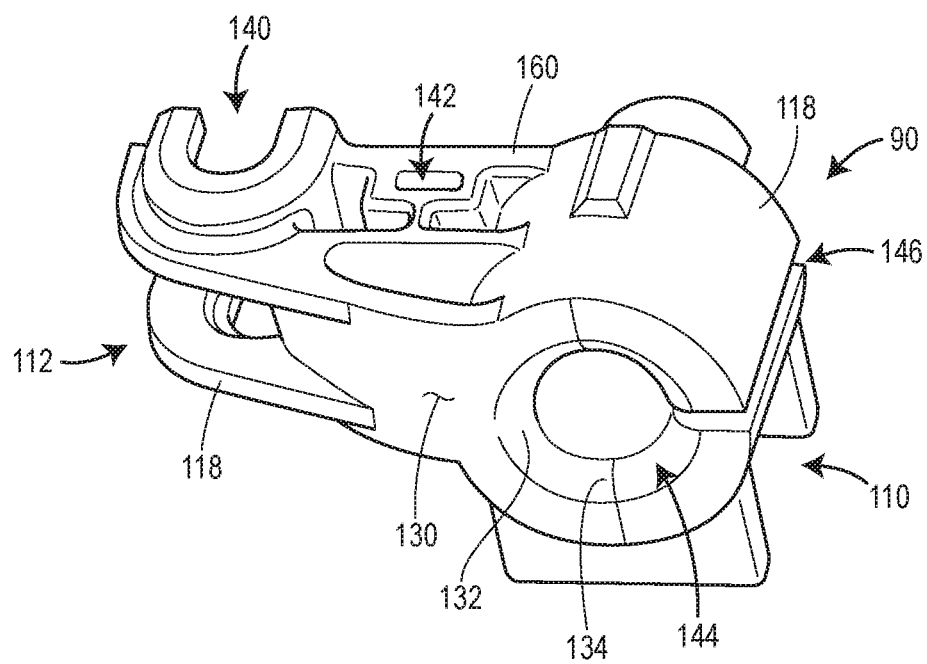
FIG. 6 is a perspective view of the drive housing of the drive assembly illustrated in FIG. 4 shown in isolation.
Figure 7:
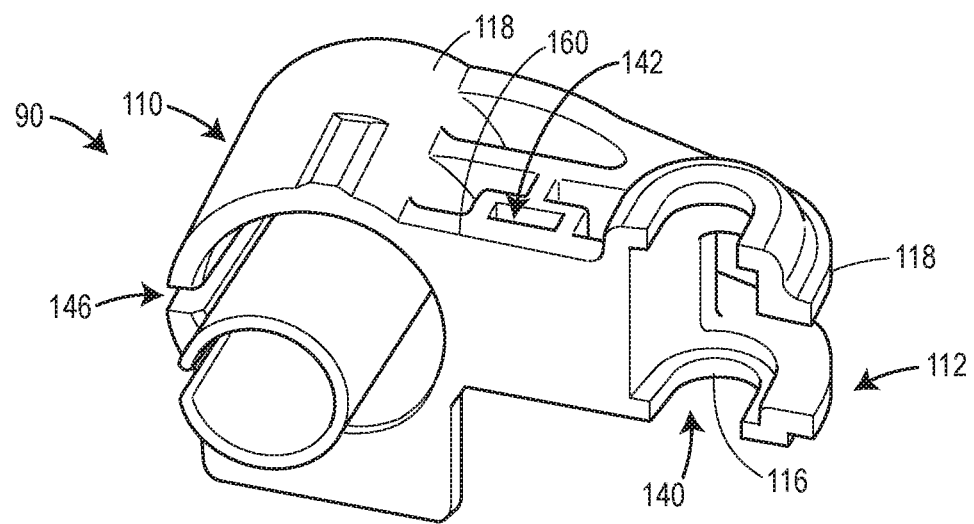
FIG. 7 is another perspective view of the drive housing shown in FIG. 6.

Referring to FIGS. 6 and 7, several openings may be formed in the exterior surface 118 of the drive housing 90 for various purposes. A first opening 140 may be formed in the exterior surface 118 of the second end 112 of the drive housing 90, and may be configured to receive the capstan 86. In some embodiments, the first opening 140 may be sized and/or dimensioned to allow the capstan 86 to be installed within the drive housing 90 by moving the capstan 86 through the first opening 140 in a direction that is perpendicular or otherwise non-parallel to the rotational axis A3 of the capstan 86. To facilitate this type of installation of the capstan 86, a length of the first opening 140 may be greater than or equal to an axial length of the capstan 86, in some embodiments. The first opening 140 may advantageously allow the capstan 86 to inserted laterally from the side or horizontally into the drive housing 90. This may provide flexibility in the process of assembling the drive assembly 24, as the capstan 86 need not necessarily be inserted in an axial or vertical direction into the drive housing 90. In some embodiments, such as the one illustrated in FIGS. 6 and 7, the first opening 140 may be formed on a side of the drive housing 90 opposite to a side of the drive housing 90 including the guide surface 130.

With continued reference to FIGS. 6 and 7, a second opening 142 may be formed in an upwardly facing portion 160 of the exterior surface 118 of the drive housing 90. The second opening 142 may be configured to receive and engage an end of the lock member 150 for temporarily limiting (e.g., preventing) rotation of the of the capstan 86 relative to the drive housing 90 during assembly of the drug delivery device 10, as illustrated in FIG. 8. In some embodiments, the second opening 142 may extend into the drive housing 90 in a direction that this parallel or otherwise non-perpendicular to the rotational axis A3 of the capstan 86. In some embodiments, the second opening 142 may be a through hole that extends through the entirety of the drive housing 90 and exits through a downwardly facing portion of the exterior surface 118 of the drive housing 90. In other embodiments, the second opening 142 may be a recess, groove, depression, or blind hole formed in the upwardly facing portion 160 of the exterior surface 118 of the drive housing 90. Furthermore, the second opening 142 need not necessarily be formed in the upwardly facing portion 160 of the exterior surface 118 of the drive housing 90. In some embodiments, the second opening 142 may be formed in a laterally facing portion of the exterior surface 118 of the drive housing 90.

Turning briefly to FIG. 8, illustrated is an embodiment of the lock member 150. The lock member 150 may have a first end 152 sized and dimensioned to be slidably received within the opening 128 in the capstan 86, and a second end 154 sized and dimensioned to be slidably received within the second opening 142 formed in the drive housing 90. In the illustrated, the embodiment of the lock member 150 is generally U-shaped; however, other shapes are also possible for the lock member 150. The opening 128 and the first end 152 of the lock member 150 may be configured such that the capstan 86 cannot rotate relative to the lock member 150 about the rotational axis A3 when the first end 152 of the lock member 150 is received within the opening 128. In some embodiments, this may be achieved by constructing each of the opening 128 and the first end 152 of the lock member 150 with a non-circular cross-section. For example, in the illustrated embodiment, each of the opening 128 and the first end 152 of the lock member 150 has a rectangular cross-section. Other suitable non-circular cross-sections include a square, triangular, semicircular, or pentagonal cross-section, or any other cross-section having linear edge or side. In embodiments where the opening 128 is not centered about the rotational axis A3, the opening 128 may not require a non-circular cross section in order to prevent the capstan 86 from rotating relative to the lock member 150. Furthermore, as shown in FIG. 8, in some embodiments, the first and second ends 152 and 154 may be parallel or substantially parallel to each other.

When the first and second ends 152 and 154 of the lock member 150 are received, respectively, in the openings 128 and 142, an attempt to rotate the capstan 86 will cause the first and second ends 152 and 154 of the lock member 150 to abut against interior walls defining, respectively, the openings 128 and 142. As a result, the lock member 150 may inhibit or prevent the capstan 86 from rotating relative to the drive housing 90, which in turn may inhibit or prevent the tether 76 from being unwound from the capstan 76 by the biasing force imparted by the stopper biasing member 74. The lock member 150 may be inserted, manually or automatically by a machine, into the openings 128 and 142 to prevent the stopper biasing member 74 from expanding in the time period before the capstan 86 is connected to the output gear 84g and/or rotational power source 70. This may allow the stopper biasing member 74 to be loaded or compressed prior to installing the stopper biasing member 74 in the main housing 29. After the capstan 86 is connected to the output gear 84g and/or rotational power source 70, these component(s) may be used to prevent unintended rotation of the capstan 86 relative to the drive housing 90, and thus the lock member 150 may be removed from the openings 128 and 142 and discarded (or re-used again in the assembly process of another drug delivery device 10). The lock member 150 may be constructed of a relatively rigid material such as plastic or metal such that the lock member 150 undergoes little or no deformation when performing its locking function.

Figure 9:
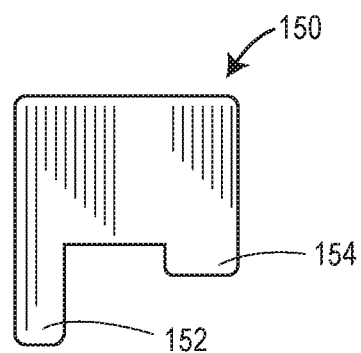
FIG. 9 is a front plan view of the lock member illustrated in FIG. 8.

In addition to this locking functionality, in some embodiments the lock member 150 may be employed as a lever for rotating the capstan 86, for example, to remove slack from the tether 76 and/or compress the stopper biasing member 74 during assembly. In such a lever configuration, the first end 152 of the lock member 150 may be inserted into the opening 128, but the second end 154 of the lock member 150 may not be inserted into the second opening 142 formed in the drive housing 90. This configuration may be achieved by constructing the lock member 150 such that the second end 154 is shorter than the first end 152, as shown in FIG. 9.

Referring back to FIGS. 6 and 7, a third opening 144 may be formed in the exterior surface 118 of the first end 110 of the drive housing 90. In some embodiments, the third opening 144 may be a through hole which extends between opposite sides of the drive housing 90. A portion or an entirety of the third opening 144 may be centered about or aligned with the longitudinal axis A2 of the stopper biasing member 74, such that at least a portion of the third opening 144 is parallel or substantially parallel to the longitudinal axis A2 of the stopper biasing member 74. The third opening 144 may generally have a circular cross-sectional shape or any other suitable cross-sectional shape. The rim 134 of the third opening 144 may be defined by a portion of the exterior surface 118 of the drive housing 90, at a location where the opening 144 intersects with the exterior surface 118 of the drive housing 90. As noted above, at least a portion of the guide surface 130 may be formed by a portion of the rim 134 of the third opening 144, in some embodiments. Furthermore, the rim 134 may be rounded so as to limit damage to and/or sliding friction with the tether 76.

Still referring to FIGS. 6 and 7, a fourth opening 146 also may be formed in the exterior surface 118 of the first end 110 of the drive housing 90. The fourth opening 146 may take the form of an elongated slot and have a generally rectangular cross-section. Furthermore, the fourth opening 146 may extend into the first end 110 of the drive housing 90 in a direction that is perpendicular or otherwise non-parallel to the longitudinal axis A2 of the stopper biasing member 74. Still further, the fourth opening 146 may communicate or intersect with the third opening 144, thereby enabling the tether 76 to be threaded or inserted into the third opening 144 laterally in a horizontal direction through a lateral side of the drive housing 90. In alternative embodiments, the fourth opening 146 may be omitted, such that the lateral side of drive housing 90 has a continuous exterior surface.

Referring back to FIG. 5, in some embodiments, an opening or slot 148 may be formed in an exterior side surface of the tether mounting member 106. The opening 148 may allow the tether 76 to be threaded or inserted into an interior of the tether mounting member 106 laterally in a horizontal direction through a lateral side of the tether mounting member 106. Although FIG. 5 illustrates the opening 148 being rotationally offset from the fourth opening 146 in the drive housing 90, alternative embodiments may have the opening 148 rotationally aligned with the fourth opening 146 in the drive housing 90. Furthermore, in some alternative embodiments, the opening 148 may be omitted, such that the lateral side of the tether mounting member 106 has a continuous exterior surface.

Prior to activation of the rotational power source 70, the tether 76 may be pulled taut between the tether mounting member 106 and the capstan 86 as a result of the stopper biasing member 74 exerting a biasing force on tether mounting member 106. In this configuration, the tether 76 may prevent the stopper biasing member 74 from moving the stopper 34 through the reservoir 30, because the tether 76 is attached to the capstan 86 which may not rotate to allow the tether 76 to unwind. During operation of the drug delivery device 10, the rotational power source 70 may be activated to rotate the capstan 86 via the gears 84a-g. As the capstan 86 rotates, the tether 76 may unwind and slack may form in the tether 76. This slack may allow the stopper biasing member 74 to expand and push the stopper 34 through the reservoir 30, thereby expelling the drug 32 from the container 14. As the stopper biasing ember 74 expands, it may pull the tether 76 over the guide surface 130, which may cause the tether 76 to change directions as described above.

Methods of assembling the drug delivery device 10 will now be described, with reference to FIGS. 1-8. As an initial step, the container 14, which may be pre-filled with the drug 32, may be installed within the main housing 29. Also, other components of the drug delivery device 10, such as the insertion mechanism 12, the fluid pathway assembly 22, and/or the controller 26, also may be installed within the main housing 29 at this initial stage. The installation of these components may involve mounting or otherwise connecting these components to the interior surface 17 of the main housing main 29. In alternative embodiments, one or more of these components may be installed within the main housing 29 after the drive assembly 24 has been installed within the main housing 29.

With regard to assembling or manufacturing the drive assembly 24, initially the second end 122 of the tether 76 may be threaded or otherwise inserted through the central opening of the stopper biasing member 74. Next, the first end 120 of tether 76 may be fastened or otherwise connected to the capstan 86 and the second end 122 of the tether 76 may be fastened or otherwise connected to the tether mounting member 106. Then, the capstan 86 may be rotatably connected to the interior surface 116 of drive housing 90. This step may involve inserting the capstan 86 through the first opening 140 formed in the drive housing 90 by moving the capstan in a direction that is perpendicular or otherwise non-parallel to the rotational axis A3 of the capstan 86. Depending on the orientation of the drive housing 90, the capstan 86 may be inserted in a horizontal direction through first opening 140 in the drive housing 90.

After rotatably mounting the capstan 86, the second end 122 of the tether 76 may be inserted through the third opening 144. In embodiments where the tether 76 has already been inserted through the stopper biasing member 74 and connected to the tether mounting member 106, this step may involve initially feeding the second end 122 of the tether 76 through the fourth opening 146 formed in the side of the drive housing 90 and subsequently pulling the tether 76 into the third opening 144 from the side. While the second end 122 of the tether 76 is inserted through the third opening 144, the tether 76 may be routed or positioned over the guide surface 130. Next, the proximal end 102 of the stopper biasing member 74 may be seated directly against the first end 110 of the drive housing 90.

After the stopper biasing member 74 has been seated, the capstan 86 may be rotated, manually or by a machine, to wind the first end 110 of the tether 76 around the capstan 86. In some embodiments, the first end 152 of the lock member 150 may be inserted into the opening 128 formed in the capstan 86 and utilized as a lever or handle for rotating the capstan 86. As the first end 110 of the tether 76 is wound around the capstan 86, the second end 112 of the tether 76 may be retracted toward the capstan 86. This may cause the second end 112 of the tether 76 to pull the tether mounting member 106 against the distal end 104 of the stopper biasing member 74, which in turn may compress the stopper biasing member 74 against the first end 110 of the drive housing 90. During such compression, the axial length of the stopper biasing member 74 along the longitudinal axis A2 may shorten. Also, winding the first end 110 of the tether 76 around the capstan 86 may pull the tether taut against the guide surface 130.

Once the stopper biasing member 74 has been sufficiently compressed, one may temporarily lock the capstan 86 in place so that it cannot rotate relative to the drive housing 90 under the biasing force of the stopper biasing member 74. In some embodiments, this may involve removably connecting the lock member 150 to the capstan 86 and the drive housing 90. In some embodiments, this may involve vertically inserting the first end 152 of the lock member 150 into the opening 128 formed in the capstan 86 and vertically inserting the second end 154 of the lock member 150 into the second opening 142 formed in the drive housing 90. This locked and loaded arrangement of the tether 76, capstan 86, drive housing 90, stopper biasing member 74, and tether mounting member 90 (see FIG. 8) may then be shipped or transferred to a location where the final assembly of the drug delivery device 10 is to occur.

Subsequently, the locked and loaded arrangement of the tether 76, capstan 86, drive housing 90, stopper biasing member 74, and tether mounting member 90 may be installed within the main housing 29 of the drug delivery device 10. In some embodiments, this installation process may involve rigidly or fixedly connecting (e.g., via fasteners) the drive housing 90, directly or indirectly, to the interior surface 17 of the main housing 29. Also, the installation process may involve operably connecting the capstan 86 to the rotational power surface 70 such that the rotational power source 70 can rotate the capstan 86 during operation of the drug delivery device 10. In some embodiments, the capstan 86 may be axially aligned with and rigidly connected to an upper surface of the output gear 86g in order to operably connect the capstan 86 to the rotational power source 70. After the capstan 86 has been operably connected to the rotational power source 70, the lock member 150 may be disconnected from the capstan 86 and the drive housing 90 by removing the first end 152 of the lock member 150 from the opening 128 in the capstan 86 and removing the second end 154 of the lock member 150 from the second opening 142 in the drive housing 90. Thereafter, rotation of the capstan 86 may be enabled or prevented depending on whether the rotational power source 70 is ON or OFF.

It should be noted that the sequence of any one of the foregoing steps of assembling the drive assembly 24 may be changed in alternative embodiments. In some alternative embodiments, the first end 120 of tether 76 may be wound around the capstan 86 prior to rotatably connecting the capstan 86 to the drive housing 90. Furthermore, in some alternative embodiments, the second end 122 of the tether 76 may be connected to the tether mounting member 106 after the second end 122 of the tether 76 is inserted through the third opening 144 in the drive housing 90.

In a final assembly stage, any openings in the main housing 29 may be sealed or otherwise closed shut, thereby enclosing the pre-filled container 14, the insertion mechanism 12, the fluid pathway assembly 22, the drive assembly 24, the controller 26, and any other internal elements of the drug delivery device 10 within the main housing 29. At the completion of the assembly process, the drug delivery device 10 may be configured as a pre-loaded and pre-filled drug delivery device.

Where appropriate, any of the above-described sub-assemblies, mechanisms, components, features, functionalities, methods of assembly or manufacture, methods of use, and other aspects of the drug delivery device 10 may be replaced with and/or combined with any of the sub-assemblies, mechanisms, components, features, functionalities, methods of manufacture or assembly, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; U.S. Provisional Patent Application No. 62/535,777 entitled "GAS PERMEABLE SEALING MEMBER FOR DRUG CONTAINER AND METHODS OF ASSEMBLY"; U.S. Provisional Patent Application No. 62/536,909 entitled "DRUG DELIVERY DEVICE WITH CONTAINER ACCESS SYSTEM AND RELATED METHOD OF ASSEMBLY"; U.S. Provisional Patent Application No. 62/536,911 entitled "DRUG DELIVERY DEVICE WITH GEAR MODULE AND RELATED METHOD OF ASSEMBLY"; U.S. Provisional Patent Application No. 62/547,500 entitled "WEARABLE INJECTOR WITH STERILE ADHESIVE PATCH"; U.S. Provisional Patent Application No. 62/548,750 entitled "NEEDLE INSERTION MECHANISM FOR DRUG DELIVERY DEVICE"; International Patent Application No. PCT/US2017/017627 entitled "DRUG DELIVERY DEVICE, METHOD OF MANUFACTURE, AND METHOD OF USE"; International Patent Application No. PCT/US2017/026524 entitled "DRUG DELIVERY DEVICE, METHOD OF MANUFACTURE, AND METHOD OF USE"; International Patent Application Publication No. WO/2016/130679 entitled "ROTATIONALLY BIASED INSERTION MECHANISM FOR A DRUG DELIVERY PUMP"; International Patent Application Publication No. WO/2016/141082 entitled "DEVICE AND METHOD FOR MAKING ASEPTIC CONNECTIONS"; and International Patent Application Publication No. WO/2016/145094 entitled "DRIVE MECHANISMS FOR DRUG DELIVERY PUMPS".

Drug Information

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-$\alpha 4\beta 7$ mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA.

Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
    a main housing including an exterior surface releasably attachable to a patient;
    a container disposed in the main housing and containing a drug and a stopper; and
    a drive assembly including
        a drive housing having a guide surface and an opening,
        a tether slidably engaging the guide surface of the drive housing and having a first end and a second end,
        a capstan rotatable relative to the drive housing about a rotational axis, the first end of the tether being wound around the capstan,
        a stopper biasing member operably connected to the second end of the tether and having a longitudinal axis aligned with the opening in the drive housing, the stopper biasing member being initially retained in an energized state by the tether and configured to expand to move the stopper through the container when released from the energized state, and
        the tether being pulled taut against the guide surface of the drive housing by the stopper biasing member,
    wherein a rim of the opening formed in the drive housing defines at least a portion of the guide surface.

2. The drug delivery device of claim 1, the drive housing having a first end operably connected to the stopper biasing member and a second end housing the capstan, the guide surface being positioned between the first end of the drive housing and the second end of the drive housing.

3. The drug delivery device of claim 1, the stopper biasing member being configured to expand along a longitudinal axis, the rotational axis of the capstan being spaced apart from the longitudinal axis.

4. The drug delivery device of claim 3, the rotational axis of the capstan being perpendicular to the longitudinal axis.

5. The drug delivery device of claim 1, the drive housing including a first opening allowing the capstan to be installed within the drive housing by moving the capstan through the first opening in a direction that is non-parallel to the rotational axis of the capstan.

6. The drug delivery device of claim 1, the drive housing including a second opening configured to receive a lock member for temporarily limiting rotation of the capstan relative to the drive housing.

7. The drug delivery device of claim 1, wherein the tether changes directions when sliding over the guide surface during operation of the drug delivery device, such that a first portion of the tether upstream of the guide surface moves in a first direction and a second portion of the tether downstream of the guide surface moves in a second direction.

8. The drug delivery device of claim 7, the rotational axis of the capstan being non-parallel to the first direction and non-parallel to the second direction.

9. The drug delivery device of claim 1, comprising a rotational power source operably connected to the capstan and configured to selectively rotate the capstan to create slack in the tether to regulate expansion of the stopper biasing member.

10. A drive assembly for a drug delivery device, the drive assembly comprising:
a drive housing having a guide surface and an opening, a rim of the opening formed in the drive housing defines at least a portion of the guide surface;
a tether slidably engaging the guide surface of the drive housing and having a first end and a second end;
a capstan rotatable relative to the drive housing about a rotational axis, the first end of the tether being wound around the capstan;
a biasing member operably connected to the second end of the tether and having a longitudinal axis aligned with the opening in the drive housing, the biasing member being initially retained in an energized state by the tether and configured to expand to move when released from the energized state; and
the tether being pulled taut against the guide surface of the drive housing by the biasing member.

11. The drive assembly of claim 10, the drive housing having a first end operably connected to the biasing member and a second end housing the capstan, the guide surface being positioned between the first end of the drive housing and the second end of the drive housing.

12. The drive assembly of claim 10, the drive housing including a first opening allowing the capstan to be installed within the drive housing by moving the capstan through the first opening in a direction that is non-parallel to the rotational axis of the capstan.

13. The drive assembly of claim 12, the first opening and the guide surface being formed on opposite sides of the drive housing.

14. The drive assembly of claim 10, the drive housing including a second opening configured to receive a lock member for temporarily limiting rotation of the capstan relative to the drive housing.

* * * * *